US012721291B2

(12) United States Patent
Ligthart et al.

(10) Patent No.: US 12,721,291 B2
(45) Date of Patent: Sep. 1, 2026

(54) ALBUGO-CANDIDA-RESISTANT BRASSICA OLERACEA PLANTS

(71) Applicant: Bejo Zaden B.V., Warmenhuizen (NL)

(72) Inventors: Johannes Theodorus Wilhelmus Ligthart, Warmenhuizen (NL); Jan Sybe Wijngaarden, Warmenhuizen (NL); Johannes Gerardus Maria Hoogland, Warmenhuizen (NL); Hubertus Theodorus Maria Janssen, Warmenhuizen (NL); Roelof Marinus Veenstra, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 170 days.

(21) Appl. No.: 18/278,516

(22) PCT Filed: Feb. 24, 2021

(86) PCT No.: PCT/EP2021/054588

§ 371 (c)(1),
(2) Date: Aug. 23, 2023

(87) PCT Pub. No.: WO2022/179682

PCT Pub. Date: Sep. 1, 2022

(65) Prior Publication Data

US 2024/0049667 A1 Feb. 15, 2024

(51) Int. Cl.

| | |
|---|---|
| ***C12Q 1/68*** | (2018.01) |
| ***A01H 1/00*** | (2006.01) |
| ***A01H 1/02*** | (2006.01) |
| ***A01H 6/20*** | (2018.01) |
| ***C12Q 1/6895*** | (2018.01) |

(52) U.S. Cl.

CPC ........... *A01H 1/1255* (2021.01); *A01H 1/023* (2021.01); *A01H 6/203* (2018.05); *C12Q 1/6895* (2013.01); *C12Q 2600/13* (2013.01)

(58) Field of Classification Search

None

See application file for complete search history.

(56) References Cited

U.S. PATENT DOCUMENTS

| | | | | |
|---|---|---|---|---|
| 9,320,211 | B2 * | 4/2016 | Linders ................ | C12Q 1/6895 |
| 2011/0030085 | A1 | 2/2011 | De Geus et al. | |
| 2012/0185960 | A1 * | 7/2012 | Linders ................ | C12Q 1/6895 536/23.6 |

FOREIGN PATENT DOCUMENTS

| | | |
|---|---|---|
| WO | 2011036108 A1 | 3/2011 |

OTHER PUBLICATIONS

Haun et al. Plant Physiology (2011), vol. 155, pp. 645-655.*
Großkinsky et al. Journal of Experimental Botany (2015), vol. 66(18), pp. 5429-5440.*
EMBL, 0099974 Brassica napus Cold acclimation—light Brassica napus cDNA, mRNA sequence, Jul. 8, 2007.

* cited by examiner

*Primary Examiner* — Medina A Ibrahim
(74) *Attorney, Agent, or Firm* — The Webb Law Firm

(57) ABSTRACT

Provided herein are *Brassica oleracea* plants being resistant to the plant pathogen *Albugo candida* and wherein the resistance is encoded by one genomic region on chromosome. Also provided herein are methods for identifying the present *Albugo candida* resistance and to molecular markers for use in the present methods.

9 Claims, No Drawings

Specification includes a Sequence Listing.

ALBUGO-CANDIDA-RESISTANT BRASSICA OLERACEA PLANTS

CROSS-REFERENCE TO RELATED APPLICATION

This application is the United States national phase of International Application No. PCT/EP2021/054588 filed Feb. 24, 2021, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2305748_ST25.txt. The size of the text file is 19,021 bytes, and the text file was created on Jul. 20, 2023.

BACKGROUND OF THE INVENTION

Field of the Invention

The present invention relates to *Brassica oleracea* plants being resistant to the plant pathogen *Albugo candida* and wherein the resistance is encoded by one genomic region on chromosome 2. The present invention further relates to methods for identifying the present *Albugo candida* resistance and to molecular markers for use in the present methods.

Description of Related Art

Cabbage, or *Brassica oleracea*, is grown globally as a food crop. Almost every part of the *B. oleracea* plant is suitable for consumption. Several cultivars of *B. oleracea* exist, including headed cabbage, savoy cabbage, borecole and point headed cabbage (edible part: the leaves); broccoli, sprouting broccoli, Romanesco and cauliflower (edible part: the flower heads); Brussels sprouts (edible part: the lateral buds) and kohlrabi (edible part: the hypocotyl which looks like a thickened part of the stem of the plant). All of these vegetables are rich in essential nutrients, including vitamin C. A diet rich in cruciferous vegetables can reduce the risk of developing some types of human cancers.

As is the case for many cultivated crops, several diseases and pests pose a threat to the cultivation of *B. oleracea*. Among these is the oomycete *Albugo candida*, which causes a disease called white blister. This plant disease causes blisters with spores (sari, pustules) on the leaves, stems and ovaries (siliques) of *Brassica* plants. These blisters may merge together to form larger, irregular shaped lesions. Systemic infection of a plant results in abnormal growth, deformations and sometimes sterility of the flowers or inflorescence.

White blister or *A. candida* (other synonyms: *A. cruciferum, A. cruciferatum*, white rust, white blister rust, staghead) is an oomycete closely related to downy mildew (*Peronospora parasitica*) and *Phytophthora*.

The oomycete *A. candida* occurs in many parts of the world where plants belonging to the family of Brassicaceae (formerly referred to as Cruciferae) are grown, including Europe, Asia, Africa, Australasia, North, Central, and South America.

The spores of the oomycete are dispersed by wind, rain and insects to other plants, but also watering, farm equipment and farm workers can contribute to the spread of *A. candida*.

When spores of *A. candida* land on a *Brassica* plant, they form a germ tube with which they penetrate the leaf. After leaf penetration, the mycelium grows intercellularly and absorbs nutrients via haustoria. The mycelium also develops zoosporangia just beneath the epidermis of the host in which asexual spores called zoospores form. When there is enough moisture, the mature zoospores are released and spread to other plants to cause new infections. The spores have two whiplash tails (flagella), one to move forward and one to control swimming direction.

The oomycete *A. candida* thrives best at temperatures between and 10 and 20° C. and in moist conditions. A leaf wetness period of 2.5 hours is enough to result in infection with the first symptoms appearing after an incubation period of 10 to 14 days. Moist weather conditions with moderate temperatures are therefore ideal conditions for the disease to spread.

*A. candida* can overwinter in the ground in sexual form as thick-walled oospores on plant remnants, or in asexual form (mycelium) on winter-hardened host plants. During mild winters the oomycete does not become dormant but remains active at a lower level.

Besides *B. oleracea, A. candida* can also infect species related to *B. oleracea*, such as rape, mustard and radish, and wild species, such as shepherd's purse (*Capsella bursa-pastoris*) and wild mustard (charlock mustard, *Sinapis arvensis*).

Host specialization in *A. candida* is known and different physiological species and *formae* speciales are distinguished based on the plant species or the line that is infected and the aggressiveness of the isolate on this particular plant species or line.

Currently, only few agents can control white blister in Brassicas. Moreover, an increasing number of countries in Europe have a policy aimed at reducing the use of crop protection agents. If the use of control agents would no longer be allowed, this would lead to significant problems in the cultivation of *Brassica* crops. White blister can cause enormous losses in yield, especially in crops such as *Brassica rapa* (syn. *campestris*) (turnip rape), *Brassica juncea* (mustard) and *Brassica napus* (rapeseed). Moreover, in vegetable crops, like broccoli, Brussels sprouts, headed cabbage and curly kale, cosmetic damage caused by the infection will make the crop no longer marketable.

Considering the problems outlined above, it is a goal for (vegetable) plant breeding to develop resistant plants harbouring one or more resistance genes or genetic loci contributing to resistance to this pathogen. This approach also contributes to the more sustainable production of the crop involved. In general, resistance can be monogenic, i.e., determined by one locus or gene, or depend on several loci or genes. In the latter case, these genes can be additive, resulting in Quantitative Trait Loci or QTLs.

The availability of marker sequences linked to the resistance gene or genes contributes to the acceleration of the breeding process as *B. oleracea* is a biannual crop Linking specific DNA markers to a resistance gene makes it possible to identify resistant plants in the offspring of various crosses. The use of DNA markers allows the researcher to directly test the seedling for the presence of a particular resistance without the need for time-consuming field tests. As a result, the biannual life cycle of *B. oleracea* no longer limits the ability of the researcher to test for resistance to *A. candida*. Hence, the use of DNA markers to select for desirable traits referred to as marker-assisted breeding makes it possible to rapidly introduce a resistance gene from one parental line to several *B. oleracea* crops.

In general, breeding for resistance starts by making a cross between a source of resistance and susceptible genetic material with a high level of agronomical quality. Resistant offspring is selected using DNA markers and repeatedly backcrossed to the agronomically elite parent line. This process ultimately leads to resistant plants with desirable agronomic characteristics. Application of cell biological techniques, such as doubled haploid induction (anther culture or microspore culture), can accelerate breeding by giving a high level of genetic purity within one generation.

SUMMARY OF THE INVENTION

Considering the above, it is an object of the present invention, amongst others, to provide novel *Albugo candida*-resistance-providing genomic fragments and plants comprising these fragments.

The present invention meets the above object, amongst other objects, as outlined in the appended claims.

Specifically, this object, amongst other objects, is achieved by providing *Brassica oleracea* plants wherein the plants are resistant to the plant pathogen *Albugo candida*, and wherein the resistance is encoded by one genomic region located on chromosome 2 between base pairs 5373001 and 6058829.

DESCRIPTION OF THE INVENTION

Although the present genomic fragment can be introduced into *Brassica oleracea* plants by introgression, the genomic fragment can be artificially introduced in plant cells to generate *Albugo candida*-resistant plants using various genome engineering techniques.

As the genomic region is known, the genomic fragment can, for example, be transferred between plants using microplast-mediated chromosome transfer. Using this method, entire chromosomes or parts thereof can be horizontally transferred between plants. First, micro-protoplasts containing one or a few chromosomes that carry the resistance are generated. Subsequently, the micro-protoplasts are fused with protoplasts generated from a susceptible *Brassica oleracea* plant. This method produces plants with monosomic additions, which can subsequently be crossed with other plants to generate *Albugo candida*-resistant lines.

Alternatively, as the nucleotide sequences of the present genomic fragment is known, these fragments can also be artificially assembled in yeast and subsequently allowed to recombine with the *Brassica oleracea* genome. Sections of the genomic fragment can also be amplified by long-range PCR amplifications or de novo synthesized and the resulting fragments reassembled and transformed into *Brassica oleracea* cells in a single step or in a series of transformations ultimately resulting in the present *Brassica oleracea* plants. The present genomic fragment, completely or in parts later to be reassembled, can also be isolated from gels or columns, for example, after restriction digestion, and subsequently transformed into *Brassica oleracea* cells.

Yet alternatively, the genomic fragment of interest can be introduced into a vector under a (strong) promotor. Subsequently, susceptible plants can be transformed with the vector and the sequence of interest expressed resulting in resistance. These techniques are readily available for the skilled person. Construction of artificial chromosomes comprising the present genomic fragments is also contemplated within the context of the present invention.

According to a preferred embodiment of the present invention, the present genomic region is obtainable, obtained, or is from a *Brassica oleracea* plant resistant to *Albugo candida* comprising one genomic region located on chromosome 2 from base pairs 5373001 to 6058829 deposited at NCIMB (National Collections of Industrial, Food and Marine Bacteria; NCIMB Limited, Ferguson Building; Craibstone Estate, Bucksburn Aberdeen, Scotland, AB21 9YA United Kingdom) on 6 Aug. 2019 under number NCIMB 43452.

The present *Brassica oleracea* plants preferably comprise one or more genomic sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, and SEQ ID No. 43. The odd SEQ ID numbers represent the sequences corresponding to the resistance allele, while the even SEQ ID numbers represent the sequences corresponding to the susceptible allele. Hence, SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 38, SEQ ID No. 40, SEQ ID No. 42, and SEQ ID No. 44 represent the sequences corresponding to the susceptible allele.

According to a preferred embodiment, the present *Brassica oleracea* plants are cytoplasmic male sterile (CMS).

According to yet another preferred embodiment, the present *Brassica oleracea* plants are hybrid plants.

Preferably, the present *Brassica oleracea* plants are selected from the group consisting of *Brassica oleracea* convar. *botrytis* var. *botrytis* (cauliflower, Romanesco), *Brassica oleracea* convar. *botrytis* var. *cymosa* (broccoli), *Brassica oleracea* convar. *botrytis* var. *asparagoides* (sprouting broccoli), *Brassica oleracea* convar. *oleracea* var. *gemnifera* (Brussels sprouts), *Brassica oleracea* convar. *capitata* var. *alba* (white cabbage, oxheart cabbage), *Brassica oleracea* convar. *capitata* var. *rubra* (red cabbage), *Brassica oleracea* convar. *capitata* var. *sabauda* (savoy cabbage), *Brassica oleracea* convar. *acephela* var. *sabellica* (curly kale cabbage), *Brassica oleracea* convar. *acephela* var. *gongylodes* (turnip cabbage) and *Brassica oleracea* var. tronchuda syn. *costata* (Portuguese cabbage).

The present invention also relates to hybrid *Brassica oleracea* plants obtainable either by crossing *Albugo candida*-susceptible *Brassica oleracea* plants with *Brassica oleracea* plants comprising the present *Albugo candida* resistance or by crossing an *Albugo candida*-susceptible *Brassica oleracea* plant with deposit NCIMB 43452.

According to an especially preferred embodiment of the present invention, the present resistance providing genomic fragment is obtainable, obtained or derived from a *Brassica* plant of which representative seeds are deposited under NCIMB 43452 on 6 Aug. 2019 at the NCIMB (NCIMB Limited, Ferguson Building; Craibstone Estate, Bucksburn ABERDEEN, Scotland, AB21 9YA United Kingdom).

Within the context of the present invention the following *B. oleracea* plant are contemplated. *B. oleracea* convar. *botrytis* var. *botrytis* (cauliflower, Romanesco), *B. oleracea* convar. *botrytis* var. *cymosa* (broccoli), *B. oleracea* convar. *botrytis* var. *asparagoides* (sprouting broccoli), *B. oleracea* convar. *oleracea* var. *gemnifera* (Brussels sprouts), *B. oleracea* convar. *capitata* var. *alba* (white cabbage, point headed cabbage), *B. oleracea* convar. *capitata* var. *rubra* (red cabbage), *B. oleracea* convar. *capitata* var. *sabauda* (savoy cabbage), *B. oleracea* convar. *acephala* var. *sabellica* (borecole), *B. oleracea* convar. *acephela* var. *gongylodes* (kohlrabi) and *B. oleracea* var. tronchuda syn. *costata* (Portuguese cabbage).

The present invention further relates to methods for identifying the genomically-encoded resistance against the plant pathogen *Albugo candida* as found in the *Brassica oleracea* plant deposited under deposit number NCIMB 43452, the method comprises the step of detecting the presence of one or more genomic sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, and SEQ ID No. 43.

The present invention further also relates to seeds or plant parts of plants defined above or to seeds capable of providing the present plants and to molecular markers which markers co-segregate with the genomically-encoded resistance against the plant pathogen *Albugo candida* as present in deposit NCIMB 43452.

The present invention furthermore relates to molecular markers which markers co-segregate with a genomically encoded resistance against the plant pathogen *Albugo candida* as present in deposit NCIMB 43452, which molecular markers are selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, and SEQ ID No. 43.

The present invention will be further detailed in the following examples.

EXAMPLES

Example 1. Populations and Disease Test

The white blister resistance originates from the parent line 947354 of Bejo Zaden B.V. of which seeds were deposited at the NCIMB (NCIMB Limited, Ferguson Building; Craibstone Estate, Bucksburn ABERDEEN, Scotland, AB21 9YA, United Kingdom) on 6 Aug. 2019 under number NCIMB 43452.

This source was crossed with different *B. oleracea* species (curly kale, cabbage, turnip cabbage, broccoli, sprouting broccoli, white cabbage, oxheart cabbage, red cabbage, savoy cabbage, tronchuda, Brussels sprouts and cauliflower). BC1 populations were obtained after backcrossing with susceptible parent lines. Resistant plants were selected from these populations using a disease test.

Isolates of *A. candida* were obtained by isolating zoosporangia from susceptible *B. oleracea* plants in the field. After germination in water, the spores were used to inoculate susceptible plants. After the development of blisters, these zoosporangia were harvested and stored in liquid nitrogen until use.

The disease test took place in a glasshouse on seedlings of the BC1 population 24 to 48 hours after development of the seed leaves. The plants were inoculated with a fresh zoospore suspension $5\times10^4$ zoospores per ml) which was prepared by washing zoosporangia from susceptible plants and allowing them to germinate in water. Several drops of zoospore suspension were pipetted onto the seed leaves. After this procedure, the plants were grown under a plastic tunnel to guarantee optimal conditions for infection. Two weeks after inoculation, the plants were assessed by grouping them in three classes: resistant, susceptible or intermediate. After performing the disease test on the seedlings, the resistant plants were retained for the backcrossing program.

The results of the disease test showed that the resistance was, in principle, a monogenic dominant trait. Plants with intermediate reactions were, however, also often found in addition to susceptible and resistant plants. The presence of plants with an intermediate resistance was found to be highly dependent on the genetic background of the plants. Several populations were selected for the breeding program that had no, or hardly any, intermediate resistance and in which the expected segregation ratio (1:1 for a BC and 3:1 for self-pollination) was found.

Example 2. Molecular Characterization of Genomic DNA and Mapping of the Resistance Gene Several backcross populations were produced by crossing and repeated backcrossing of the source of resistance, deposited as NCIMB 43452 and a variety of *B. oleracea* cultivars. A set of SNP markers was subsequently developed by comparing sequence data from lines susceptible and resistant to *A. candida*. These SNP markers were repeatedly mapped on different *Brassica* populations. By selecting crossovers, the mapped region was narrowed down to the markers listed in Table 1.

The analysis of several generations of plants made it possible to reduce the genetic location of the resistance gene to an area of ~465.000 bp, which corresponds to approx. 0.7% of this chromosome. Many SNP markers are in this area, enabling precise and rapid identification of plants harbouring the gene resulting in resistance to *A. candida.*

The locus defining *A. candida* resistance was determined to be on chromosome 2, and the positions of the SNP markers developed are found in Table 2. Abbreviations are according to IUPAC nucleotide code:

| Symbol | Nucleotide Base |
|---|---|
| A | Adenine |
| C | Cytosine |
| G | Guanine |
| T | Thymine |
| N | A or C or G or T |
| M | A or C |
| R | A or G |
| W | A or T |
| S | C or G |
| Y | C or T |
| K | G or T |
| V | Not T |
| H | Not G |
| D | Not C |
| B | Not A |

TABLE 1

SNPs for the detection of resistance against *A. candida*. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SNP | KSNP | Position on Chromosome 2 (bp) | Allele linked to resistance | Alternative allele |
|---|---|---|---|---|
| 1 | 1009-4271.1 | 5373001 | T | C |
| 2 | 1009-4273.1 | 5385215 | A | G |
| 3 | 1009-4281.1 | 5697266 | T | G |
| 4 | 1009-4294.1 | 5453680 | C | G |
| 5 | 1009-2712.1 | 5455211 | T | C |
| 6 | 1009-0673.1 | 5481017 | T | C |
| 7 | 1009-0672.1 | 5480996 | C | T |
| 8 | 1009-2710.1 | 5487235 | A | C |
| 9 | 1009-2709.1 | 5514066 | G | A |
| 10 | 1009-2707.1 | 5518162 | T | C |
| 11 | 1009-0106.1 | 5559368 | T | A |
| 12 | 1009-0663.1 | 5559789 | A | G |

TABLE 1-continued

SNPs for the detection of resistance against *A. candida*. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SNP | KSNP | Position on Chromosome 2 (bp) | Allele linked to resistance | Alternative allele |
|---|---|---|---|---|
| 13 | 1009-2705.1 | 5573298 | A | G |
| 14 | 1009-6115.1 | 5740881 | G | T |
| 15 | 1009-6153.1 | 5750175 | A | G |
| 16 | 1009-6154.1 | 5766914 | T | G |
| 17 | 1009-6199.1 | 5776195 | G | C |
| 18 | 1009-6155.1 | 5791347 | C | T |
| 19 | 1009-6157.1 | 5840760 | A | G |
| 20 | 1009-6161.1 | 5933093 | A | C |
| 21 | 1009-2703.1 | 6007107 | C | T |
| 22 | 1009-2701.1 | 6058829 | G | A |

TABLE 2

Sequence and position on chromosome 2 of SNPs used for the detection of resistance against *A. candida*. Sequences with odd numbers are linked to resistance to *A. candida*, whereas sequences with even numbers to susceptibility. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SEQ ID No. | Position on Chr 2 (bp) | Sequence (SNP nucleotide is bold and in brackets) |
|---|---|---|
| 1 | 5373001 | AAAAAATATGGAGTGAAATACAAAGATTAAATTAATAAATAGAATGA<br>AACAATAAAGATTCAGACCAAAACCTATCAACCAACTAAGCAACCAG<br>ACATGC[**T**]MGAACMARAAAAATYGRGGATAGTCGAAGTCRARAACAA<br>TGCAHCACAATACCGAGARAWAAKTGTTCTCAAACCTTGAAACAAYTC<br>CTTCTACAGCYKC |
| 2 | 5373001 | AAAAAATATGGAGTGAAATACAAAGATTAAATTAATAAATAGAATGA<br>AACAATAAAGATTCAGACCAAAACCTATCAACCAACTAAGCAACCAG<br>ACATGC[**C**]MGAACMARAAAAATYGRGGATAGTCGAAGTCRARAACAA<br>TGCAHCACAATACCGAGARAWAAKTGTTCTCAAACCTTGAAACAAYTC<br>CTTCTACAGCYKC |
| 3 | 5385215 | ATCGAATAATGTAATTTGTATTTTTATAAATTTAATTTCACTCAATAYA<br>YATATATATGATATAGTCATATAGACGTGGYTTGGCAGAAAAAGAKGG<br>AGA[**A**]CACACTCATGGTTWATAGAAAAAGAGGGAACAAAGTAATAGC<br>GAGGTTGTCCYWTTCTTCTTGATCARTGATTATSRATCKGTTTCGTAGT<br>GCTCTTGTT |
| 4 | 5385215 | ATCGAATAATGTAATTTGTATTTTTATAAATTTAATTTCACTCAATAYA<br>YATATATATGATATAGTCATATAGACGTGGYTTGGCAGAAAAAGAKGG<br>AGA[**G**]CACACTCATGGTTWATAGAAAAAGAGGGAACAAAGTAATAGC<br>GAGGTTGTCCYWTTCTTCTTGATCARTGATTATSRATCKGTTTCGTAGT<br>GCTCTTGTT |
| 5 | 5697266 | CATATCATAAAAGCTAATGGAAGTAAATGGGAACSAACCATCTSCGAG<br>ARTCATAACCAGCTATATTGGCGACACCCTCCAAAGCTTCCCTCCATGC<br>CTT[**T**]ACCTTTTCTTCTTTCCCCACAGGTTTTTTCAAAGGCTTTCCCG<br>AAATCTCCGGTCTGCTTCCTAACMTCAGATGGATCCACTTCGTAGAAAA<br>TGGATATC |
| 6 | 5697266 | CATATCATAAAAGCTAATGGAAGTAAATGGGAACSAACCATCTSCGAG<br>ARTCATAACCAGCTATATTGGCGACACCCTCCAAAGCTTCCCTCCATGC<br>CTT[**G**]ACCTTTTCTTCTTTCCCCACAGGTTTTTTCAAAGGCTTTCCCG<br>AAATCTCCGGTCTGCTTCCTAACMTCAGATGGATCCACTTCGTAGAAAA<br>TGGATATC |
| 7 | 5453680 | AAAAACAAATACAAGAAATGTACCAACTGTTAAGCCAAGAAATCTGA<br>GAACACATAATGTCAGAGGCTCAGAGCACGAGCACGAGTATTTCACAT<br>AACTA[**C**]AAGATGGTGTTAAAAGATTTACCAAAATAAATGCATTTGGC |

TABLE 2-continued

Sequence and position on chromosome 2 of SNPs used for the detection of resistance against *A. candida*. Sequences with odd numbers are linked to resistance to *A. candida*, whereas sequences with even numbers to susceptibility. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SEQ ID No. | Position on Chr 2 (bp) | Sequence (SNP nucleotide is bold and in brackets) |
|---|---|---|
| | | ATATACGGAAGGAATAATTAGAAATACAAATCTAAGAAATTTATTTGA<br>GTTRAMAAAAA |
| 8 | 5453680 | AAAAACAAATACAAGAAATGTACCAACTGTTAAGCCAAGAAATCTGA<br>GAACACATAATGTCAGAGGCTCAGAGCACGAGCACGAGTATTTCACAT<br>AACTA[**G**]AAGATGGTGTTAAAAGATTTACCAAAATAAATGCATTTGGC<br>ATATACGGAAGGAATAATTAGAAATACAAATCTAAGAAATTTATTTGA<br>GTTRAMAAAAA |
| 9 | 5455211 | AACTTGAGTTATTTCATTCTCATGTACTCGAACACATACATCTTGAGAA<br>CTGAATAATATAGTATAAACGAATAAAACTGAACTTAGGGATTGCTCA<br>AAC[**T**]GAGTTTCCCACTTCATCATGTGTGGCTCATAGGGCAAGAGCAG<br>AGCTAAGGTTCATAGGGTTCATATACTTGGTGGTACCGGTCAATATATG<br>ACGGACTA |
| 10 | 5455211 | AACTTGAGTTATTTCATTCTCATGTACTCGAACACATACATCTTGAGAA<br>CTGAATAATATAGTATAAACGAATAAAACTGAACTTAGGGATTGCTCA<br>AAC[**C**]GAGTTTCCCACTTCATCATGTGTGGCTCATAGGGCAAGAGCAG<br>AGCTAAGGTTCATAGGGTTCATATACTTGGTGGTACCGGTCAATATATG<br>ACGGACTA |
| 11 | 5481017 | ACCTCCTCGCTGATGACCTTTTCGAGAATCATCCAAGGAGGATGACTCT<br>GTATGAACTGACAGTTTCTTTCCATGTTGATGCACCGAAAACAAGAAG<br>CAACCAAACAAAAGAAAGAAGATTGTAAAAGTCCATTCRTACACCAA<br>GATCAAACCAGTCCATGGCATGATTTGCCTCGGCAYAATCACAAAGGA<br>AGTTCCAA[**T**]GGATATCAGAAGTGCAGTAAAACAGACTAGAACTGAA<br>ACTGCGCCTAAGCGCTGAGGAACTTTGGAGTGTATGCTGCCACTGTGG<br>AGTTGATAGCTGGGATACATGGTTGAAAATGTAGAAACACCGCGTGTT<br>CCATTAGATCTGATTCTGTAATAAAGATATCTAATCTGATTGAATAATG<br>AACCCTCATGAACCTGAA |
| 12 | 5481017 | ACCTCCTCGCTGATGACCTTTTCGAGAATCATCCAAGGAGGATGACTCT<br>GTATGAACTGACAGTTTCTTTCCATGTTGATGCACCGAAAACAAGAAG<br>CAACCAAACAAAAGAAAGAAGATTGTAAAAGTCCATTCRTACACCAA<br>GATCAAACCAGTCCATGGCATGATTTGCCTCGGCAYAATCACAAAGGA<br>AGTTCCAA[**C**]GGATATCAGAAGTGCAGTAAAACAGACTAGAACTGAA<br>ACTGCGCCTAAGCGCTGAGGAACTTTGGAGTGTATGCTGCCACTGTGG<br>AGTTGATAGCTGGGATACATGGTTGAAAATGTAGAAACACCGCGTGTT<br>CCATTAGATCTGATTCTGTAATAAAGATATCTAATCTGATTGAATAATG<br>AACCCTCATGAACCTGAA |
| 13 | 5480996 | TGTAGTAACGTCACAAGACACACCTCCTCGCTGATGACCTTTTCGAGA<br>ATCATCCAAGGAGGATGACTCTGTATGAACTGACAGTTTCTTTCCATGT<br>TGATGCACCGAAAACAAGAAGCAACCAAACAAAAGAAAGAAGATTGT<br>AAAAGTCCATTCRTACACCAAGATCAAACCAGTCCATGGCATGATTTG<br>CCTCGGCA[**C**]AATCACAAAGGAAGTTCCAAYGGATATCAGAAGTGCA<br>GTAAAACAGACTAGAACTGAAACTGCGCCTAAGCGCTGAGGAACTTTG<br>GAGTGTATGCTGCCACTGTGGAGTTGATAGCTGGGATACATGGTTGAA<br>AATGTAGAAACACCGCGTGTTCCATTAGATCTGATTCTGTAATAAAGA<br>TATCTAATCTGATTGAATA |
| 14 | 5480996 | TGTAGTAACGTCACAAGACACACCTCCTCGCTGATGACCTTTTCGAGA<br>ATCATCCAAGGAGGATGACTCTGTATGAACTGACAGTTTCTTTCCATGT<br>TGATGCACCGAAAACAAGAAGCAACCAAACAAAAGAAAGAAGATTGT<br>AAAAGTCCATTCRTACACCAAGATCAAACCAGTCCATGGCATGATTTG<br>CCTCGGCA[**T**]AATCACAAAGGAAGTTCCAAYGGATATCAGAAGTGCAG<br>TAAAACAGACTAGAACTGAAACTGCGCCTAAGCGCTGAGGAACTTTGG<br>AGTGTATGCTGCCACTGTGGAGTTGATAGCTGGGATACATGGTTGAAA<br>ATGTAGAAACACCGCGTGTTCCATTAGATCTGATTCTGTAATAAAGAT<br>ATCTAATCTGATTGAATA |
| 15 | 5487235 | TCAAGAACGACCATCCCGTTCCGATCAAGATGATCACGGTGAAAAGCA<br>ACACGACACGAATGAATTGGAAGATGTAGAAGAGGATGTCCCATCCGT<br>GAGG[**A**]GTCCCCGTGATCTTCACGTARTGCTTATCYTCAGCTGCGCAGA<br>TCAGATTCAAAGACTTGATTAAAAGCAGACCCGCCATGAGGAGATGGA<br>TCC |

TABLE 2-continued

Sequence and position on chromosome 2 of SNPs used for the detection of resistance against *A. candida*. Sequences with odd numbers are linked to resistance to *A. candida*, whereas sequences with even numbers to susceptibility. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SEQ ID No. | Position on Chr 2 (bp) | Sequence (SNP nucleotide is bold and in brackets) |
|---|---|---|
| 16 | 5487235 | TCAAGAACGACCATCCCGTTCCGATCAAGATGATCACGGTGAAAAGCA ACACGACACGAATGAATTGGAAGATGTAGAAGAGGATGTCCCATCCGT GAGG[**C**]GTCCCCGTGATCTTCACGTARTGCTTATCYTCAGCTGCGCAGA TCAGATTCAAAGACTTGATTAAAAGCAGACCCGCCATGAGGAGATGGA TCC |
| 17 | 5514066 | GAGATGGAGTTGGTGTGGCATGACTCAGCCAATGGYTCGAGCCGTCCT ACAAATTCGAACAAGACTTCYACAGACTCAGTTAGATGGCCTCAATGG AAGT[**G**]AACCAACMGAGAAGTGAATATGATTACGTTTCCGGTTCAGTG GATTAACCAACAGGTTGCAGATCATTGAATCGATATGTTTGTATGTTTA AATATAATA |
| 18 | 5514066 | GAGATGGAGTTGGTGTGGCATGACTCAGCCAATGGYTCGAGCCGTCCT ACAAATTCGAACAAGACTTCYACAGACTCAGTTAGATGGCCTCAATGG AAGT[**A**]AACCAACMGAGAAGTGAATATGATTACGTTTCCGGTTCAGTG GATTAACCAACAGGTTGCAGATCATTGAATCGATATGTTTGTATGTTTA AATATAATA |
| 19 | 5518162 | GTTTCTATAAGAAGAAACCAGAAGAAGGGTCTATTAGTGGAAGGGTCC AGAGGCTTGCDAAGTATCGATTCTTGAAGAAACAATCGGATCTKTTGT TGAA[**T**]TCTGATGATTTGGCTGCTATGTGGAATTGTCTGAGAGAAAATT GTGTGATTGATGATGCCACTGGTGCTGAAAAGATGAACTATGAAGACT TCTGCCACA |
| 20 | 5518162 | GTTTCTATAAGAAGAAACCAGAAGAAGGGTCTATTAGTGGAAGGGTCC AGAGGCTTGCDAAGTATCGATTCTTGAAGAAACAATCGGATCTKTTGT TGAA[**C**]TCTGATGATTTGGCTGCTATGTGGAATTGTCTGAGAGAAAATT GTGTGATTGATGATGCCACTGGTGCTGAAAAGATGAACTATGAAGACT TCTGCCACA |
| 21 | 5559368 | TCACGCATGACCATGATATTGTTCCTCATCTGCCTCCTTACTACAACCA TTTTCCTCAAAAAACATACCACCACTTCCCAACAGAGGTGTGGCTAAG AGATGTC[**T**]GTTCCTTGAATCATAGTGTGGAGAAAGTTTGTGACAACA CCGGTGAAGATCCAACATGCAGCAGGTCGGTGAAGGGCAATAGCATTT CAGACCATCTAAGGTACTTTGGGGTAGAGTTGCATTGTGAGACTTGGA GACAATGCTCAATAGTGATGAGCCATGAGATGGATAGATTCAGCAAGA AGGATTCAAAGGGTAAT |
| 22 | 5559368 | TCACGCATGACCATGATATTGTTCCTCATCTGCCTCCTTACTACAACCA TTTTCCTCAAAAAACATACCACCACTTCCCAACAGAGGTGTGGCTAAG AGATGTC[**A**]GTTCCTTGAATCATAGTGTGGAGAAAGTTTGTGACAACA CCGGTGAAGATCCAACATGCAGCAGGTCGGTGAAGGGCAATAGCATTT CAGACCATCTAAGGTACTTTGGGGTAGAGTTGCATTGTGAGACTTGGA GACAATGCTCAATAGTGATGAGCCATGAGATGGATAGATTCAGCAAGA AGGATTCAAAGGGTAAT |
| 23 | 5559789 | CATAGTGTGGAGAAAGTTTGTGACAACACCGGTGAAGATCCAACATGC AGCAGGTCGGTGAAGGGCAATAGCATTTCAGACCATCTAAGGTACTTT GGGGTAGAGTTGCATTGTGAGACTTGGAGACAATGCTCAATAGTGATG AGCCATGAGATGGATAGATTCAGCAAGAAGGATTCAAAGGGTAATCTA ATCATGTC[**A**]CGGAATGTTCCTTCCACCAACGGTAACAAAACAGAATC TCTTATCGAAAATGGGGATCTTTAGTCTATAGGAATCGTTGATTCAAGT CTTGGTCAAGCAAAGCTTGCTTCAAAAGGAGATTCCGGTGTTGGAGAA AGAAAGAAAGTGTATAGATACATATAATCAAGACTTTGTAAATAGGTT GTAGGTTGATAGTACGT |
| 24 | 5559789 | CATAGTGTGGAGAAAGTTTGTGACAACACCGGTGAAGATCCAACATGC AGCAGGTCGGTGAAGGGCAATAGCATTTCAGACCATCTAAGGTACTTT GGGGTAGAGTTGCATTGTGAGACTTGGAGACAATGCTCAATAGTGATG AGCCATGAGATGGATAGATTCAGCAAGAAGGATTCAAAGGGTAATCTA ATCATGTC[**G**]CGGAATGTTCCTTCCACCAACGGTAACAAAACAGAATC TCTTATCGAAAATGGGGATCTTTAGTCTATAGGAATCGTTGATTCAAGT CTTGGTCAAGCAAAGCTTGCTTCAAAAGGAGATTCCGGTGTTGGAGAA AGAAAGAAAGTGTATAGATACATATAATCAAGACTTTGTAAATAGGTT GTAGGTTGATAGTACGT |

TABLE 2-continued

Sequence and position on chromosome 2 of SNPs used for the detection of resistance against *A. candida*. Sequences with odd numbers are linked to resistance to *A. candida*, whereas sequences with even numbers to susceptibility. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SEQ ID No. | Position on Chr 2 (bp) | Sequence (SNP nucleotide is bold and in brackets) |
|---|---|---|
| 25 | 5573298 | CCTTTGTACTAAACCACTTAATGGCACAGTGCTCATGAACGAGCCTGA GGTCACCTTTGCAACTGCATTCCATTTTCAACGTGTTGCCTTCCTCGCA GAC[**A**]TCAAGACAAATCCTGCACACCGCTTCTTCTTCAGGGATCTCTTC TTCAGTTTCTTCCGCAGTAACCGGAGTGATTTCATCTCCACAACCACTT GCTTCAT |
| 26 | 5573298 | CCTTTGTACTAAACCACTTAATGGCACAGTGCTCATGAACGAGCCTGA GGTCACCTTTGCAACTGCATTCCATTTTCAACGTGTTGCCTTCCTCGCA GAC[**G**]TCAAGACAAATCCTGCACACCGCTTCTTCTTCAGGGATCTCTTC TTCAGTTTCTTCCGCAGTAACCGGAGTGATTTCATCTCCACAACCACTT GCTTCAT |
| 27 | 5740881 | TTAGGTGTCAGGTCCYGGGTTGTGAAGTGGATATAAGCGAGCTCAAAG GGTAYCATARAAGGCATAGGGTTTGYCTCACGTGTGCTAACGCTAGCT CCGT[**G**]GTGCTTGAGGGAGTGGATAAGAGATACTGTCAACAGTGTGGA AAGTAWGTTCCTTTTATTGTTAATTTGATCCTATGCTTTATGGCTTAAC AGATACATA |
| 28 | 5740881 | TTAGGTGTCAGGTCCYGGGTTGTGAAGTGGATATAAGCGAGCTCAAAG GGTAYCATARAAGGCATAGGGTTTGYCTCACGTGTGCTAACGCTAGCT CCGT[**T**]GTGCTTGAGGGAGTGGATAAGAGATACTGTCAACAGTGTGGA AAGTAWGTTCCTTTTATTGTTAATTTGATCCTATGCTTTATGGCTTAAC AGATACATA |
| 29 | 5750175 | TCAACAGTCTCAACTCTACGGTTCAAACACCTGAATCTCAGTTTGTGCA CCGGTTGCTCGACAGACTACATGCTCTCCATCAGGATCACATGAGCTA CAA[**A**]CATGTGGTTGAAAAGCCTTTTAGTTTTCCGCTTCCTAATAARGA TGATCTTGTCTGGTTTTTAAACAAACCCTTTTAACTGTTGTTCCAGGGG ATGTTCT |
| 30 | 5750175 | TCAACAGTCTCAACTCTACGGTTCAAACACCTGAATCTCAGTTTGTGCA CCGGTTGCTCGACAGACTACATGCTCTCCATCAGGATCACATGAGCTA CAA[**G**]CATGTGGTTGAAAAGCCTTTTAGTTTTCCGCTTCCTAATAARGA TGATCTTGTCTGGTTTTTAAACAAACCCTTTTAACTGTTGTTCCAGGGG ATGTTCT |
| 31 | 5766914 | AACCATAATCTGGAGAMTTTTGACCAAAAGCATATTGACASAAGATCT GCAGAGCCCAAGTTGAAGCTGGAAATATCATCTCATACATATGGTTGG TCCY[**T**]AGTCCCAGTGACTTGAGAAGTTTTTTATCTTCGGTTGTAATGA TAACAATACTTCCCGGACCAACCCATCCACGCTGGTTTGCCATCTCCTC TAATTGYC |
| 32 | 5766914 | AACCATAATCTGGAGAMTTTTGACCAAAAGCATATTGACASAAGATCT GCAGAGCCCAAGTTGAAGCTGGAAATATCATCTCATACATATGGTTGG TCCY[**G**]AGTCCCAGTGACTTGAGAAGTTTTTTATCTTCGGTTGTAATGA TAACAATACTTCCCGGACCAACCCATCCACGCTGGTTTGCCATCTCCTC TAATTGYC |
| 33 | 5776195 | TTTGAATTCCACAAGATTAGCTATACARYATTACTTTTTGAAACTAAAC TAAGTTATATTGTAACGCATGACSGGCTACAGYTAATGGACTTTCCACG CT[**G**]ACTCACTCKGTTGGTGTGCTTCATATGCGTGCGCATGGCGGTATA TTAATTTTTTGGAGGCTCCTARGACTTGTYTATTAACTCTTAATCAACC ACRTRA |
| 34 | 5776195 | TTTGAATTCCACAAGATTAGCTATACARYATTACTTTTTGAAACTAAAC TAAGTTATATTGTAACGCATGACSGGCTACAGYTAATGGACTTTCCACG CT[**C**]ACTCACTCKGTTGGTGTGCTTCATATGCGTGCGCATGGCGGTATA TTAATTTTTTGGAGGCTCCTARGACTTGTYTATTAACTCTTAATCAACC ACRTRA |
| 35 | 5791347 | CGAGGAGTTGTACTTTTTTCTTTGTAAACAATATTTGCTTGCGCAATAA ATTGAACATTCCCGAAAATAACCTATCGCTTTTACCCCTAAAAAAAATT AC[**C**]GCCAAAAAGTTGAAGCATGACATATTTAGGTCCGAGTCTTCTTCT TCGTCTCAATATATATTGTGGGGCCAGCAATTTGGTGGGAACCGTCGA CGTGGAA |

TABLE 2-continued

Sequence and position on chromosome 2 of SNPs used for the detection of resistance against *A. candida*. Sequences with odd numbers are linked to resistance to *A. candida*, whereas sequences with even numbers to susceptibility. The reference genome was the updated assembly of the *Brassica oleracea* reference genome, JZS v2 (Cai et al., Improved *Brassica oleracea* JZS assembly reveals significant changing of LTR-RT dynamics in different morphotypes, Theoretical and Applied Genetics 2020).

| SEQ ID No. | Position on Chr 2 (bp) | Sequence (SNP nucleotide is bold and in brackets) |
|---|---|---|
| 36 | 5791347 | CGAGGAGTTGTACTTTTTTCTTTGTAAACAATATTTGCTTGCGCAATAA ATTGAACATTCCCGAAAATAACCTATCGCTTTTACCCCTAAAAAAAATT AC[**T**]GCCAAAAAGTTGAAGCATGACATATTTAGGTCCGAGTCTTCTTCT TCGTCTCAATATATATTGTGGGGCCAGCAATTTGGTGGGAACCGTCGA CGTGGAA |
| 37 | 5840760 | ACCCCAACACATTGCCTTGATGTTGAAATTAATTAATCACTATCCGTGT TCARTATTGTCTCTCCAGSCAAGTAAGTATTTGATTTTAATCATACTTTA A[**A**]TTTACAYTGCTCTTGGCCGCCTAGAAGAAACATAACAATTCAGGC CTTTGATCTTGACCYCGTTCGAAAATAGGCTCTTCTGCTGTGAACCAAA GGAGTA |
| 38 | 5840760 | ACCCCAACACATTGCCTTGATGTTGAAATTAATTAATCACTATCCGTGT TCARTATTGTCTCTCCAGSCAAGTAAGTATTTGATTTTAATCATACTTTA A[**G**]TTTACAYTGCTCTTGGCCGCCTAGAAGAAACATAACAATTCAGGC CTTTGATCTTGACCYCGTTCGAAAATAGGCTCTTCTGCTGTGAACCAAA GGAGTA |
| 39 | 5933093 | TGCCTCGATCTTGACATRARCTATATTGATGTCTGTCAGATTCTTTGTGT ATTCATCTGTCTYCTTARGCTCACCAATCAACCCAGSAGCRAAGCTTMG A[**A**]CTTCAAGGCTACGCAAGTTGAGAGGAAGACCAATCAAGTGAGCCC ACAKAGGGATCGACTCCATATCTGGAGTGGAGGCCTCGTGCTTGGAGG TCAACGR |
| 40 | 5933093 | TGCCTCGATCTTGACATRARCTATATTGATGTCTGTCAGATTCTTTGTGT ATTCATCTGTCTYCTTARGCTCACCAATCAACCCAGSAGCRAAGCTTMG A[**C**]CTTCAAGGCTACGCAAGTTGAGAGGAAGACCAATCAAGTGAGCCC ACAKAGGGATCGACTCCATATCTGGAGTGGAGGCCTCGTGCTTGGAGG TCAACGR |
| 41 | 6007107 | ATTCACGAGCAGCTTCATTAACAGAAATCCGGCAAGGAGGAGGGTTTC TTCTTGTGTCTACTGATATTGCAGCAAGGGGGATTGATCTACCGGAAAC AAC[**C**]CACATCTTCAACTTTGATCTCCCACAGACAGCTACAGATTATCT TCACCGAGCTGGAAGAGCTGGTCGAAAACCCTTTTCGGATAGGAAGTG CATTGTTA |
| 42 | 6007107 | ATTCACGAGCAGCTTCATTAACAGAAATCCGGCAAGGAGGAGGGTTTC TTCTTGTGTCTACTGATATTGCAGCAAGGGGGATTGATCTACCGGAAAC AAC[**T**]CACATCTTCAACTTTGATCTCCCACAGACAGCTACAGATTATCT TCACCGAGCTGGAAGAGCTGGTCGAAAACCCTTTTCGGATAGGAAGTG CATTGTTA |
| 43 | 6058829 | CCACCGTCCTCCTAGGRCTAGCMAGCGCRAGCTTCCTCTTCCACGGCTC CTTRAACGAAACATCAGGGATGGAGCCGCGCGTGGGGATTACGCGCCA CGT[**G**]GGGATGAGATTAGCCACGACGAAGAGCAAATGCTCCAACGGC CACGGCGGBTTGAACTTCCTGCTGATCCCRCACATGGCGCCGTTGAGG AHGAGCCCGT |
| 44 | 6058829 | CCACCGTCCTCCTAGGRCTAGCMAGCGCRAGCTTCCTCTTCCACGGCTC CTTRAACGAAACATCAGGGATGGAGCCGCGCGTGGGGATTACGCGCCA CGT[**A**]GGGATGAGATTAGCCACGACGAAGAGCAAATGCTCCAACGGC CACGGCGGBTTGAACTTCCTGCTGATCCCRCACATGGCGCCGTTGAGG AHGAGCCCGT |

The invention claimed is:

1. A cultivated *Brassica oleracea* plant resistant to the plant pathogen *Albugo candida*, wherein the resistance is encoded by one genomic region located on chromosome 2 between base pairs 5373001 and 6058829 of the *Brassica oleracea* reference genome JZS v2, wherein said plant comprises in its genome SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, and SEQ ID No. 43.

2. The *Brassica oleracea* plant according to claim 1, wherein said genomic region is obtained or is from a *Brassica oleracea* plant deposited under deposit number NCIMB 43452.

3. The *Brassica oleracea* plant according to claim 1, wherein said plant is cytoplasmic male sterile (CMS).

4. The *Brassica oleracea* plant according to claim 1, wherein said plant is a hybrid plant.

5. The *Brassica oleracea* plant according to claim 1, wherein said plant is a *Brassica oleracea* plant deposited under deposit number NCIMB 43452.

6. The *Brassica oleracea* plant according to claim 1, wherein the plant is selected from the group consisting of *Brassica oleracea* convar. *botrytis* var. *botrytis, Brassica oleracea* convar. *botrytis* var. *cymosa, Brassica oleracea* convar. *botrytis* var. *asparagoides, Brassica oleracea* convar. *oleracea* var. *gemnifera, Brassica oleracea* convar. *capitata* var. *alba, Brassica oleracea* convar. *capitata* var. *rubra, Brassica oleracea* convar. *capitata* var. *sabauda, Brassica oleracea* convar. *acephela* var. *sabellica, Brassica oleracea* convar. *acephela* var. *gongylodes* and *Brassica oleracea* var. tronchuda syn. *costata.*

7. A method for producing a *Brassica oleracea* plant that is resistant to the plant pathogen *Albugo candida*, the method comprising:

detecting in a genome of a first plant SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, and SEQ ID No. 43;

crossing the first plant with a second plant to produce offspring; and selecting offspring that are resistant to *Albugo candida.*

8. A seed or plant part of the *Brassica oleracea* plant according to claim 1 and comprising in its genome a genomic region located on chromosome 2 between base pairs 5373001 and 6058829 of the *Brassica oleracea* reference genome JZS v2 and SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37, SEQ ID No. 39, SEQ ID No. 41, and SEQ ID No. 43.

9. A seed that produces the hybrid plant according to claim 4.

* * * * *

SEQUENCE LISTING

<160> NUMBER OF SEQ ID NOS: 44

<210> SEQ ID NO 1
<211> LENGTH: 201
<212> TYPE: DNA
<213> ORGANISM: Brassica oleracea

<400> SEQUENCE: 1

```
aaaaaatatg gagtgaaata caaagattaa attaataaat agaatgaaac aataaagatt     60

cagaccaaaa cctatcaacc aactaagcaa ccagacatgc tmgaacmara aaaatygrgg    120

atagtcgaag tcraraacaa tgcahcacaa taccgagara waaktgttct caaaccttga    180

aacaaytcct tctacagcyk c                                              201
```

<210> SEQ ID NO 2
<211> LENGTH: 201
<212> TYPE: DNA
<213> ORGANISM: Brassica oleracea

<400> SEQUENCE: 2

```
aaaaaatatg gagtgaaata caaagattaa attaataaat agaatgaaac aataaagatt     60

cagaccaaaa cctatcaacc aactaagcaa ccagacatgc cmgaacmara aaaatygrgg    120

atagtcgaag tcraraacaa tgcahcacaa taccgagara waaktgttct caaaccttga    180

aacaaytcct tctacagcyk c                                              201
```

<210> SEQ ID NO 3
<211> LENGTH: 201
<212> TYPE: DNA
<213> ORGANISM: Brassica oleracea

<400> SEQUENCE: 3

```
atcgaataat gtaatttgta tttttataaa tttaatttca ctcaatayay atatatatga     60

tatagtcata tagacgtggy ttggcagaaa aagakggaga acacactcat ggttwataga    120

aaaagaggga acaaagtaat agcgaggttg tccywttctt cttgatcart gattatsrat    180

ckgtttcgta gtgctcttgt t                                              201
```

<210> SEQ ID NO 4
<211> LENGTH: 201
<212> TYPE: DNA
<213> ORGANISM: Brassica oleracea

<400> SEQUENCE: 4

```
atcgaataat gtaatttgta tttttataaa tttaatttca ctcaatayay atatatatga     60

tatagtcata tagacgtggy ttggcagaaa aagakggaga gcacactcat ggttwataga    120

aaaagaggga acaaagtaat agcgaggttg tccywttctt cttgatcart gattatsrat    180

ckgtttcgta gtgctcttgt t                                              201
```

<210> SEQ ID NO 5
<211> LENGTH: 201
<212> TYPE: DNA
<213> ORGANISM: Brassica oleracea

<400> SEQUENCE: 5

```
catatcataa aagctaatgg aagtaaatgg gaacsaacca tctscgagar tcataaccag     60

ctatattggc gacaccctcc aaagcttccc tccatgcctt taccttttct tctttcccca    120

caggtttttt caaaggcttt cccgaaatct ccggtctgct tcctaacmtc agatggatcc    180

acttcgtaga aaatggatat c                                              201
```

<210> SEQ ID NO 6
<211> LENGTH: 201
<212> TYPE: DNA

<213> ORGANISM: Brassica oleracea

<400> SEQUENCE: 6

```
catatcataa aagctaatgg aagtaaatgg gaacsaacca tctscgagar tcataaccag     60

ctatattggc gacaccctcc aaagcttccc tccatgcctt gaccttttct tctttcccca    120

caggtttttt caaaggcttt cccgaaatct ccggtctgct tcctaacmtc agatggatcc    180

acttcgtaga aaatggatat c                                              201
```

<210> SEQ ID NO 7
<211> LENGTH: 201
<212> TYPE: DNA
<213> ORGANISM: Brassica oleracea

<400> SEQUENCE: 7

```
aaaaacaaat acaagaaatg taccaactgt taagccaaga aatctgagaa cacataatgt     60

cagaggctca gagcacgagc acgagtattt cacataacta caagatggtg ttaaaagatt    120

taccaaaata aatgcatttg gcatatacgg aaggaataat tagaaataca aatctaagaa    180

atttatttga gttramaaaa a                                              201
```

<210> SEQ ID NO 8
<211> LENGTH: 201
<212> TYPE: DNA
<213> ORGANISM: Brassica oleracea

<400> SEQUENCE: 8

```
aaaaacaaat acaagaaatg taccaactgt taagccaaga aatctgagaa cacataatgt     60

cagaggctca gagcacgagc acgagtattt cacataacta gaagatggtg ttaaaagatt    120

taccaaaata aatgcatttg gcatatacgg aaggaataat tagaaataca aatctaagaa    180

atttatttga gttramaaaa a                                              201
```

<210> SEQ ID NO 9
<211> LENGTH: 201
<212> TYPE: DNA
<213> ORGANISM: Brassica oleracea

<400> SEQUENCE: 9

```
aacttgagtt atttcattct catgtactcg aacacataca tcttgagaac tgaataatat     60

agtataaacg aataaaactg aacttaggga ttgctcaaac tgagtttccc acttcatcat    120

gtgtggctca tagggcaaga gcagagctaa ggttcatagg gttcatatac ttggtggtac    180

cggtcaatat atgacggact a                                              201
```

<210> SEQ ID NO 10
<211> LENGTH: 201
<212> TYPE: DNA
<213> ORGANISM: Brassica oleracea

<400> SEQUENCE: 10

```
aacttgagtt atttcattct catgtactcg aacacataca tcttgagaac tgaataatat     60

agtataaacg aataaaactg aacttaggga ttgctcaaac cgagtttccc acttcatcat    120

gtgtggctca tagggcaaga gcagagctaa ggttcatagg gttcatatac ttggtggtac    180

cggtcaatat atgacggact a                                              201
```

<210> SEQ ID NO 11
<211> LENGTH: 401

<212> TYPE: DNA
<213> ORGANISM: Brassica oleracea

<400> SEQUENCE: 11

```
acctcctcgc tgatgacctt ttcgagaatc atccaaggag gatgactctg tatgaactga     60

cagtttcttt ccatgttgat gcaccgaaaa caagaagcaa ccaaacaaaa gaaagaagat    120

tgtaaaagtc cattcrtaca ccaagatcaa accagtccat ggcatgattt gcctcggcay    180

aatcacaaag gaagttccaa tggatatcag aagtgcagta aaacagacta gaactgaaac    240

tgcgcctaag cgctgaggaa ctttggagtg tatgctgcca ctgtggagtt gatagctggg    300

atacatggtt gaaaatgtag aaacaccgcg tgttccatta gatctgattc tgtaataaag    360

atatctaatc tgattgaata atgaaccctc atgaacctga a                        401
```

<210> SEQ ID NO 12
<211> LENGTH: 401
<212> TYPE: DNA
<213> ORGANISM: Brassica oleracea

<400> SEQUENCE: 12

```
acctcctcgc tgatgacctt ttcgagaatc atccaaggag gatgactctg tatgaactga     60

cagtttcttt ccatgttgat gcaccgaaaa caagaagcaa ccaaacaaaa gaaagaagat    120

tgtaaaagtc cattcrtaca ccaagatcaa accagtccat ggcatgattt gcctcggcay    180

aatcacaaag gaagttccaa cggatatcag aagtgcagta aaacagacta gaactgaaac    240

tgcgcctaag cgctgaggaa ctttggagtg tatgctgcca ctgtggagtt gatagctggg    300

atacatggtt gaaaatgtag aaacaccgcg tgttccatta gatctgattc tgtaataaag    360

atatctaatc tgattgaata atgaaccctc atgaacctga a                        401
```

<210> SEQ ID NO 13
<211> LENGTH: 401
<212> TYPE: DNA
<213> ORGANISM: Brassica oleracea

<400> SEQUENCE: 13

```
tgtagtaacg tcacaagaca cacctcctcg ctgatgacct tttcgagaat catccaagga     60

ggatgactct gtatgaactg acagtttctt tccatgttga tgcaccgaaa acaagaagca    120

accaaacaaa agaaagaaga ttgtaaaagt ccattcrtac accaagatca aaccagtcca    180

tggcatgatt tgcctcggca caatcacaaa ggaagttcca ayggatatca gaagtgcagt    240

aaaacagact agaactgaaa ctgcgcctaa gcgctgagga actttggagt gtatgctgcc    300

actgtggagt tgatagctgg gatacatggt tgaaaatgta gaaacaccgc gtgttccatt    360

agatctgatt ctgtaataaa gatatctaat ctgattgaat a                        401
```

<210> SEQ ID NO 14
<211> LENGTH: 401
<212> TYPE: DNA
<213> ORGANISM: Brassica oleracea

<400> SEQUENCE: 14

```
tgtagtaacg tcacaagaca cacctcctcg ctgatgacct tttcgagaat catccaagga     60

ggatgactct gtatgaactg acagtttctt tccatgttga tgcaccgaaa acaagaagca    120

accaaacaaa agaaagaaga ttgtaaaagt ccattcrtac accaagatca aaccagtcca    180

tggcatgatt tgcctcggca taatcacaaa ggaagttcca ayggatatca gaagtgcagt    240
```

```
aaaacagact agaactgaaa ctgcgcctaa gcgctgagga actttggagt gtatgctgcc    300

actgtggagt tgatagctgg gatacatggt tgaaaatgta gaaacaccgc gtgttccatt    360

agatctgatt ctgtaataaa gatatctaat ctgattgaat a                        401


<210> SEQ ID NO 15
<211> LENGTH: 195
<212> TYPE: DNA
<213> ORGANISM: Brassica oleracea

<400> SEQUENCE: 15

tcaagaacga ccatcccgtt ccgatcaaga tgatcacggt gaaaagcaac acgacacgaa     60

tgaattggaa gatgtagaag aggatgtccc atccgtgagg agtccccgtg atcttcacgt    120

artgcttatc ytcagctgcg cagatcagat tcaaagactt gattaaaagc agacccgcca    180

tgaggagatg gatcc                                                     195


<210> SEQ ID NO 16
<211> LENGTH: 195
<212> TYPE: DNA
<213> ORGANISM: Brassica oleracea

<400> SEQUENCE: 16

tcaagaacga ccatcccgtt ccgatcaaga tgatcacggt gaaaagcaac acgacacgaa     60

tgaattggaa gatgtagaag aggatgtccc atccgtgagg cgtccccgtg atcttcacgt    120

artgcttatc ytcagctgcg cagatcagat tcaaagactt gattaaaagc agacccgcca    180

tgaggagatg gatcc                                                     195


<210> SEQ ID NO 17
<211> LENGTH: 201
<212> TYPE: DNA
<213> ORGANISM: Brassica oleracea

<400> SEQUENCE: 17

gagatggagt tggtgtggca tgactcagcc aatggytcga gccgtcctac aaattcgaac     60

aagacttcya cagactcagt tagatggcct caatggaagt gaaccaacmg agaagtgaat    120

atgattacgt ttccggttca gtggattaac caacaggttg cagatcattg aatcgatatg    180

tttgtatgtt taaatataat a                                              201


<210> SEQ ID NO 18
<211> LENGTH: 201
<212> TYPE: DNA
<213> ORGANISM: Brassica oleracea

<400> SEQUENCE: 18

gagatggagt tggtgtggca tgactcagcc aatggytcga gccgtcctac aaattcgaac     60

aagacttcya cagactcagt tagatggcct caatggaagt aaaccaacmg agaagtgaat    120

atgattacgt ttccggttca gtggattaac caacaggttg cagatcattg aatcgatatg    180

tttgtatgtt taaatataat a                                              201


<210> SEQ ID NO 19
<211> LENGTH: 201
<212> TYPE: DNA
<213> ORGANISM: Brassica oleracea

<400> SEQUENCE: 19

gtttctataa gaagaaacca gaagaagggt ctattagtgg aagggtccag aggcttgcda     60
```

agtatcgatt cttgaagaaa caatcggatc tkttgttgaa ttctgatgat ttggctgcta 120
tgtggaattg tctgagagaa aattgtgtga ttgatgatgc cactggtgct gaaaagatga 180
actatgaaga cttctgccac a 201

<210> SEQ ID NO 20
<211> LENGTH: 201
<212> TYPE: DNA
<213> ORGANISM: Brassica oleracea

<400> SEQUENCE: 20
gtttctataa gaagaaacca gaagaagggt ctattagtgg aagggtccag aggcttgcda 60
agtatcgatt cttgaagaaa caatcggatc tkttgttgaa ctctgatgat ttggctgcta 120
tgtggaattg tctgagagaa aattgtgtga ttgatgatgc cactggtgct gaaaagatga 180
actatgaaga cttctgccac a 201

<210> SEQ ID NO 21
<211> LENGTH: 305
<212> TYPE: DNA
<213> ORGANISM: Brassica oleracea

<400> SEQUENCE: 21
tcacgcatga ccatgatatt gttcctcatc tgcctcctta ctacaaccat tttcctcaaa 60
aaacatacca ccacttccca acagaggtgt ggctaagaga tgtctgttcc ttgaatcata 120
gtgtggagaa agtttgtgac aacaccggtg aagatccaac atgcagcagg tcggtgaagg 180
gcaatagcat ttcagaccat ctaaggtact ttggggtaga gttgcattgt gagacttgga 240
gacaatgctc aatagtgatg agccatgaga tggatagatt cagcaagaag gattcaaagg 300
gtaat 305

<210> SEQ ID NO 22
<211> LENGTH: 305
<212> TYPE: DNA
<213> ORGANISM: Brassica oleracea

<400> SEQUENCE: 22
tcacgcatga ccatgatatt gttcctcatc tgcctcctta ctacaaccat tttcctcaaa 60
aaacatacca ccacttccca acagaggtgt ggctaagaga tgtcagttcc ttgaatcata 120
gtgtggagaa agtttgtgac aacaccggtg aagatccaac atgcagcagg tcggtgaagg 180
gcaatagcat ttcagaccat ctaaggtact ttggggtaga gttgcattgt gagacttgga 240
gacaatgctc aatagtgatg agccatgaga tggatagatt cagcaagaag gattcaaagg 300
gtaat 305

<210> SEQ ID NO 23
<211> LENGTH: 401
<212> TYPE: DNA
<213> ORGANISM: Brassica oleracea

<400> SEQUENCE: 23
catagtgtgg agaaagtttg tgacaacacc ggtgaagatc caacatgcag caggtcggtg 60
aagggcaata gcatttcaga ccatctaagg tactttgggg tagagttgca ttgtgagact 120
tggagacaat gctcaatagt gatgagccat gagatggata gattcagcaa gaaggattca 180
aagggtaatc taatcatgtc acggaatgtt ccttccacca acggtaacaa aacagaatct 240

```
cttatcgaaa atggggatct ttagtctata ggaatcgttg attcaagtct tggtcaagca    300

aagcttgctt caaaaggaga ttccggtgtt ggagaaagaa agaaagtgta tagatacata    360

taatcaagac tttgtaaata ggttgtaggt tgatagtacg t                        401


<210> SEQ ID NO 24
<211> LENGTH: 401
<212> TYPE: DNA
<213> ORGANISM: Brassica oleracea

<400> SEQUENCE: 24

catagtgtgg agaaagtttg tgacaacacc ggtgaagatc caacatgcag caggtcggtg     60

aagggcaata gcatttcaga ccatctaagg tactttgggg tagagttgca ttgtgagact    120

tggagacaat gctcaatagt gatgagccat gagatggata gattcagcaa gaaggattca    180

aagggtaatc taatcatgtc gcggaatgtt ccttccacca acggtaacaa aacagaatct    240

cttatcgaaa atggggatct ttagtctata ggaatcgttg attcaagtct tggtcaagca    300

aagcttgctt caaaaggaga ttccggtgtt ggagaaagaa agaaagtgta tagatacata    360

taatcaagac tttgtaaata ggttgtaggt tgatagtacg t                        401


<210> SEQ ID NO 25
<211> LENGTH: 201
<212> TYPE: DNA
<213> ORGANISM: Brassica oleracea

<400> SEQUENCE: 25

cctttgtact aaaccactta atggcacagt gctcatgaac gagcctgagg tcacctttgc     60

aactgcattc cattttcaac gtgttgcctt cctcgcagac atcaagacaa atcctgcaca    120

ccgcttcttc ttcagggatc tcttcttcag tttcttccgc agtaaccgga gtgatttcat    180

ctccacaacc acttgcttca t                                              201


<210> SEQ ID NO 26
<211> LENGTH: 201
<212> TYPE: DNA
<213> ORGANISM: Brassica oleracea

<400> SEQUENCE: 26

cctttgtact aaaccactta atggcacagt gctcatgaac gagcctgagg tcacctttgc     60

aactgcattc cattttcaac gtgttgcctt cctcgcagac gtcaagacaa atcctgcaca    120

ccgcttcttc ttcagggatc tcttcttcag tttcttccgc agtaaccgga gtgatttcat    180

ctccacaacc acttgcttca t                                              201


<210> SEQ ID NO 27
<211> LENGTH: 201
<212> TYPE: DNA
<213> ORGANISM: Brassica oleracea

<400> SEQUENCE: 27

ttaggtgtca ggtccygggt tgtgaagtgg atataagcga gctcaaaggg taycataraa     60

ggcatagggt ttgyctcacg tgtgctaacg ctagctccgt ggtgcttgag ggagtggata    120

agagatactg tcaacagtgt ggaaagtawg ttccttttat tgttaatttg atcctatgct    180

ttatggctta acagatacat a                                              201


<210> SEQ ID NO 28
<211> LENGTH: 201
```

<212> TYPE: DNA
<213> ORGANISM: Brassica oleracea

<400> SEQUENCE: 28
ttaggtgtca ggtccygggt tgtgaagtgg atataagcga gctcaaaggg taycataraa 60
ggcatagggt ttgyctcacg tgtgctaacg ctagctccgt tgtgcttgag ggagtggata 120
agagatactg tcaacagtgt ggaaagtawg ttccttttat tgttaatttg atcctatgct 180
ttatggctta acagatacat a 201

<210> SEQ ID NO 29
<211> LENGTH: 201
<212> TYPE: DNA
<213> ORGANISM: Brassica oleracea

<400> SEQUENCE: 29
tcaacagtct caactctacg gttcaaacac ctgaatctca gtttgtgcac cggttgctcg 60
acagactaca tgctctccat caggatcaca tgagctacaa acatgtggtt gaaaagcctt 120
ttagttttcc gcttcctaat aargatgatc ttgtctggtt tttaaacaaa cccttttaac 180
tgttgttcca ggggatgttc t 201

<210> SEQ ID NO 30
<211> LENGTH: 201
<212> TYPE: DNA
<213> ORGANISM: Brassica oleracea

<400> SEQUENCE: 30
tcaacagtct caactctacg gttcaaacac ctgaatctca gtttgtgcac cggttgctcg 60
acagactaca tgctctccat caggatcaca tgagctacaa gcatgtggtt gaaaagcctt 120
ttagttttcc gcttcctaat aargatgatc ttgtctggtt tttaaacaaa cccttttaac 180
tgttgttcca ggggatgttc t 201

<210> SEQ ID NO 31
<211> LENGTH: 201
<212> TYPE: DNA
<213> ORGANISM: Brassica oleracea

<400> SEQUENCE: 31
aaccataatc tggagamttt tgaccaaaag catattgaca saagatctgc agagcccaag 60
ttgaagctgg aaatatcatc tcatacatat ggttggtccy tagtcccagt gacttgagaa 120 gtttttatc ttcggttgta atgataacaa tacttcccgg accaacccat ccacgctggt 180
ttgccatctc ctctaattgy c 201

<210> SEQ ID NO 32
<211> LENGTH: 201
<212> TYPE: DNA
<213> ORGANISM: Brassica oleracea

<400> SEQUENCE: 32
aaccataatc tggagamttt tgaccaaaag catattgaca saagatctgc agagcccaag 60
ttgaagctgg aaatatcatc tcatacatat ggttggtccy gagtcccagt gacttgagaa 120 gtttttatc ttcggttgta atgataacaa tacttcccgg accaacccat ccacgctggt 180
ttgccatctc ctctaattgy c 201

<210> SEQ ID NO 33

<211> LENGTH: 201
<212> TYPE: DNA
<213> ORGANISM: Brassica oleracea

<400> SEQUENCE: 33

```
tttgaattcc acaagattag ctatacarya ttactttttg aaactaaact aagttatatt     60

gtaacgcatg acsggctaca gytaatggac tttccacgct gactcactck gttggtgtgc    120

ttcatatgcg tgcgcatggc ggtatattaa ttttttggag gctcctarga cttgtytatt    180

aactcttaat caaccacrtr a                                              201
```

<210> SEQ ID NO 34
<211> LENGTH: 201
<212> TYPE: DNA
<213> ORGANISM: Brassica oleracea

<400> SEQUENCE: 34

```
tttgaattcc acaagattag ctatacarya ttactttttg aaactaaact aagttatatt     60

gtaacgcatg acsggctaca gytaatggac tttccacgct cactcactck gttggtgtgc    120

ttcatatgcg tgcgcatggc ggtatattaa ttttttggag gctcctarga cttgtytatt    180

aactcttaat caaccacrtr a                                              201
```

<210> SEQ ID NO 35
<211> LENGTH: 201
<212> TYPE: DNA
<213> ORGANISM: Brassica oleracea

<400> SEQUENCE: 35

```
cgaggagttg tactttttc tttgtaaaca atatttgctt gcgcaataaa ttgaacattc     60

ccgaaaataa cctatcgctt ttacccctaa aaaaaattac cgccaaaaag ttgaagcatg    120

acatatttag gtccgagtct tcttcttcgt ctcaatatat attgtggggc cagcaatttg    180

gtgggaaccg tcgacgtgga a                                              201
```

<210> SEQ ID NO 36
<211> LENGTH: 201
<212> TYPE: DNA
<213> ORGANISM: Brassica oleracea

<400> SEQUENCE: 36

```
cgaggagttg tactttttc tttgtaaaca atatttgctt gcgcaataaa ttgaacattc     60

ccgaaaataa cctatcgctt ttacccctaa aaaaaattac tgccaaaaag ttgaagcatg    120

acatatttag gtccgagtct tcttcttcgt ctcaatatat attgtggggc cagcaatttg    180

gtgggaaccg tcgacgtgga a                                              201
```

<210> SEQ ID NO 37
<211> LENGTH: 201
<212> TYPE: DNA
<213> ORGANISM: Brassica oleracea

<400> SEQUENCE: 37

```
accccaacac attgccttga tgttgaaatt aattaatcac tatccgtgtt cartattgtc     60

tctccagsca agtaagtatt tgattttaat catactttaa atttacaytg ctcttggccg    120

cctagaagaa acataacaat tcaggccttt gatcttgacc ycgttcgaaa ataggctctt    180

ctgctgtgaa ccaaaggagt a                                              201
```

<210> SEQ ID NO 38
<211> LENGTH: 201
<212> TYPE: DNA
<213> ORGANISM: Brassica oleracea

<400> SEQUENCE: 38
accccaacac attgccttga tgttgaaatt aattaatcac tatccgtgtt cartattgtc 60
tctccagsca agtaagtatt tgattttaat catactttaa gtttacaytg ctcttggccg 120
cctagaagaa acataacaat tcaggccttt gatcttgacc ycgttcgaaa ataggctctt 180
ctgctgtgaa ccaaaggagt a 201

<210> SEQ ID NO 39
<211> LENGTH: 201
<212> TYPE: DNA
<213> ORGANISM: Brassica oleracea

<400> SEQUENCE: 39
tgcctcgatc ttgacatrar ctatattgat gtctgtcaga ttctttgtgt attcatctgt 60
ctycttargc tcaccaatca acccagsagc raagcttmga acttcaaggc tacgcaagtt 120
gagaggaaga ccaatcaagt gagcccacak agggatcgac tccatatctg gagtggaggc 180
ctcgtgcttg gaggtcaacg r 201

<210> SEQ ID NO 40
<211> LENGTH: 201
<212> TYPE: DNA
<213> ORGANISM: Brassica oleracea

<400> SEQUENCE: 40
tgcctcgatc ttgacatrar ctatattgat gtctgtcaga ttctttgtgt attcatctgt 60
ctycttargc tcaccaatca acccagsagc raagcttmga ccttcaaggc tacgcaagtt 120
gagaggaaga ccaatcaagt gagcccacak agggatcgac tccatatctg gagtggaggc 180
ctcgtgcttg gaggtcaacg r 201

<210> SEQ ID NO 41
<211> LENGTH: 201
<212> TYPE: DNA
<213> ORGANISM: Brassica oleracea

<400> SEQUENCE: 41
attcacgagc agcttcatta acagaaatcc ggcaaggagg agggtttctt cttgtgtcta 60
ctgatattgc agcaaggggg attgatctac cggaaacaac ccacatcttc aactttgatc 120
tcccacagac agctacagat tatcttcacc gagctggaag agctggtcga aaacccttt 180 cggataggaa gtgcattgtt a 201

<210> SEQ ID NO 42
<211> LENGTH: 201
<212> TYPE: DNA
<213> ORGANISM: Brassica oleracea

<400> SEQUENCE: 42
attcacgagc agcttcatta acagaaatcc ggcaaggagg agggtttctt cttgtgtcta 60
ctgatattgc agcaaggggg attgatctac cggaaacaac tcacatcttc aactttgatc 120
tcccacagac agctacagat tatcttcacc gagctggaag agctggtcga aaacccttt 180 cggataggaa gtgcattgtt a 201

-continued

```
<210> SEQ ID NO 43
<211> LENGTH: 201
<212> TYPE: DNA
<213> ORGANISM: Brassica oleracea

<400> SEQUENCE: 43

ccaccgtcct cctaggrcta gcmagcgcra gcttcctctt ccacggctcc ttraacgaaa     60

catcagggat ggagccgcgc gtggggatta cgcgccacgt ggggatgaga ttagccacga    120

cgaagagcaa atgctccaac ggccacggcg gbttgaactt cctgctgatc ccrcacatgg    180

cgccgttgag gahgagcccg t                                              201


<210> SEQ ID NO 44
<211> LENGTH: 201
<212> TYPE: DNA
<213> ORGANISM: Brassica oleracea

<400> SEQUENCE: 44

ccaccgtcct cctaggrcta gcmagcgcra gcttcctctt ccacggctcc ttraacgaaa     60

catcagggat ggagccgcgc gtggggatta cgcgccacgt agggatgaga ttagccacga    120

cgaagagcaa atgctccaac ggccacggcg gbttgaactt cctgctgatc ccrcacatgg    180

cgccgttgag gahgagcccg t                                              201
```